(12) United States Patent
Axelgaard

(10) Patent No.: US 6,745,082 B2
(45) Date of Patent: Jun. 1, 2004

(54) CURRENT-CONTROLLING ELECTRODE WITH ADJUSTABLE CONTACT AREA

(76) Inventor: Jens Axelgaard, 811 Tumbleweed La., Fallbrook, CA (US) 92028

(*) Notice: Subject to any disclaimer, the term of this patent is extended or adjusted under 35 U.S.C. 154(b) by 203 days.

(21) Appl. No.: 10/027,557

(22) Filed: Oct. 22, 2001

(65) Prior Publication Data

US 2003/0078646 A1 Apr. 24, 2003

(51) Int. Cl.$^7$ ................................. A61N 1/04
(52) U.S. Cl. .................. 607/142; 607/152; 600/372; 600/391; 600/392; 600/394
(58) Field of Search .................. 600/362, 372, 600/386, 391–395; 607/115, 142, 152

(56) References Cited

U.S. PATENT DOCUMENTS

| | | | |
|---|---|---|---|
| 4,736,752 A | 4/1988 | Munck et al. ............... 607/152 |
| 4,926,878 A | * 5/1990 | Snedeker ..................... 607/152 |
| 5,038,796 A | 8/1991 | Axelgaard et al. ........... 607/152 |
| 5,265,579 A | * 11/1993 | Ferrari ......................... 600/385 |
| 5,566,672 A | * 10/1996 | Faasse, Jr. .................... 600/372 |
| 5,843,155 A | 12/1998 | Axelgaard ..................... 607/152 |
| 5,868,136 A | 2/1999 | Fox et al. ..................... 600/391 |
| 5,904,712 A | 5/1999 | Axelgaard ..................... 607/148 |
| 6,038,464 A | 3/2000 | Axelgaard et al. ........... 600/391 |
| 6,038,485 A | 3/2000 | Axelgaard ..................... 607/148 |
| 6,115,625 A | 9/2000 | Heard et al. .................. 600/391 |
| 6,198,955 B1 | 3/2001 | Axelgaard et al. ........... 600/391 |
| 6,263,226 B1 | 7/2001 | Axelgaard et al. ........... 600/391 |
| 6,418,333 B1 | 7/2002 | Axelgaard ..................... 600/391 |
| 6,438,428 B1 | 8/2002 | Axelgaard et al. ........... 607/152 |

* cited by examiner

*Primary Examiner*—Carl Layno
(74) *Attorney, Agent, or Firm*—Walter A. Hackler

(57) ABSTRACT

A medical electrode includes a conductive flexible member having a top side and a bottom side with a non-conductive flexible sheet covering the conductive flexible member top side. A connector in contact with the conductive flexible member bottom side is provided for establishing electrical contact with an external electrical apparatus. A conductive adhesive adhered to the conductive flexible member bottom side provides electrical conduction to a patient's skin.

21 Claims, 6 Drawing Sheets

CURRENT-CONTROLLING ELECTRODE WITH ADJUSTABLE CONTACT AREA

The present invention generally relates to electrodes and, more particularly, electrodes suitable for transcutaneous nerve and/or muscle stimulation and biological signal recording.

Medical electrodes must provide an even electrical coupling to a patient's skin over an entire surface of the electrode to effect proper coupling. Because of the curvaceous nature of the human body, it is apparent that medical electrodes for use thereon must be flexible not only for confirmation with a patient's skin contours, but also to accommodate relative movement of the patient's skin.

It is well known that inadequate flexing and shaping of the electrode to a patient's contour can result in an irritation of the patient's skin. Electrical "hot spots" due to uneven electrode-skin contact can result in a rash or a burning sensation. A sensation of burning may be felt by a patient within a few minutes after application of the electrical signals during nerve and/or muscle stimulation, while rash conditions generally take a longer period of time to develop.

In order to provide uniform electrical coupling, heretofore developed electrodes have utilized conductive fabrics and foils in combination with a conductive adhesive in order to uniformly couple electrical signals to and/or firm an electrical lead wire, or connector. A number of electrodes have provided impedance compensation for directing electrical pulses from the lead wire uniformly throughout an electrode, such as, for example, U.S. Pat. No. 5,038,796 entitled, ELECTRICAL STIMULATION ELECTRODE WITH IMPEDANCE COMPENSATION, to Axelgaard. This patent teaches the use of an electrical shunt interconnected with the lead wire for causing more uniform resistance between equally spaced apart points in the electrode.

Without this shunt, many prior art electrodes have compromised the flexibility of the electrode in order to provide adequate current densities over the entire contact area of the electrode. These electrodes typically have utilized a metallic mesh, or foil, to provide conductivity and utilize a conductive gel between the electrode and the patient's skin in order to accommodate the movement therebetween. Contact between the lead wire and the metallic mesh, or foil, is typically a point contact. Because of this, electrode contacts to medical electrodes have typically been made on a top side thereof, that is, a side opposite a side of the electrode having a conductive adhesive thereon for application to a patient.

The present invention is directed to a medical electrode having an intermediate connector, that is, a connector disposed between the conductive member and the conductive adhesive which provides yet another method for controlling the current density provided by the electrode.

SUMMARY OF THE INVENTION

A medical electrode in accordance with the present invention generally includes a conductive flexible member having a top side and a bottom side and a non-conductive flexible sheet covering the conductive flexible member top side.

A connector is provided in contact with the conductive flexible member bottom side for establishing electrical contact with external electrical apparatus.

A conductive hydrogel adhesive disposed on the conductive flexible member bottom side for adhering the electrode to a patient's skin. More particularly, the medical electrode may include a snap eyelet having a head in contact with the conductive flexible member and a shaft extending through the flexible member and a non-conductive flexible member. A snap stud is fixed to the eyelet shaft on a top side of the electrode.

The eyelet conductivity may be utilized to control the conductivity pattern of the electrode. In that regard, the eyelet head may be formed from an electrically conductive material selected to match the conductivity of the conductive flexible member or a material having a greater or lower conductivity than the conductivity of the conductive flexible member.

In one embodiment of the present invention, the connector may comprise a plurality of spaced apart snap eyelets, each having a head in a contact with the conductive flexible member and a shaft extending through the conductive flexible member and a non-conductive sheet The plurality of snap studs is provided with one each fixed to each of the plurality of snap eyelet shafts. Thus, the conductivity of the electrode is not only controlled by the material or construction of the eyelet head, but also in the relative spacing of the eyelets from one another and across the electrode. In that regard, each of the plurality of the snap eyelets may have a different conductivity or the snap eyelets may be grouped into sets of snap eyelets with each eyelet in a set having the same conductivity but different from an eyelet conductivity in a different set. These combinations can be utilized to control the current distribution provided to a user and is also a useful for providing specific conductive/current distributions for enhancing drug delivery to a patient.

The conductive flexible member may itself include a conductive film with a conductive ink pattern disposed thereon. Preferably, the ink pattern has a greater conductivity than the conductivity of the conductive film.

In one embodiment of the present invention, the conductive flexible member may comprise a conductive film with a first conductive ink pattern disposed on the member bottom side and a second ink conductive pattern disposed on the member top side. These ink patterns may be utilized in combination with eyelet placement in order to further control the current distribution and conductivity of the electrode. Such ink patterns are shown in U.S. Pat. Nos. 5,904,712, 6,038,455 and 5,843,155. These patents are to be incorporated herewith in their entirety by this specific reference thereto.

In yet another embodiment of a medical electrode in accordance with the present invention, generally includes a conductive flexible member having a top side and a bottom side. A non-conductive flexible sheet covering the conductive flexible top side is provided to prevent inadvertent contact with the conductive flexible member.

A connector provides means for establishing electrical contact with an external electrical apparatus and a conductive tape provides a means for adhering the connector means to the conductive flexible member bottom side. This unique arrangement provides for additional control over the current distribution provided by the medical electrode.

A conductive adhesive adhered to the conductive flexible member bottom side and the conductive tape provides electrical conductivity to a patient's skin. More particularly, the conductive tape may comprise a conductive backing and a conductive adhesive disposed between the conductive flexible member bottom side and the conductive backing. The conductive backing may comprise any suitable material such as a conductive polymer, a conductive fabric or a metallic foil. The flexibility of the conductive member is, of course, necessary as hereinabove described, and provides a criteria for suitability of the conductive member.

The tape conductive backing and conductive adhesive may have a conductivity less than or equal to the conductivity of the flexible member. On the other hand, the conductive backing and conductive adhesive may have a combined conductivity greater than the conductivity of the conductive flexible member.

In order to control conductivity or current distribution of the medical electrode, the conductive tape may be wider than the conductive means and, in fact, have a shape which provides a means for controlling the overall conductivity of the medical electrode. Controlling elements of the conductive tape also include the thickness of the tape which may be varied. This control over electrode conductivity may, of course, be used in combination with other known methods of controlling conductivity as hereinabove noted in U.S. Pat. Nos. 5,904,712, 6,038,485 and 5,843,156.

A method for making a medical electrode in accordance with the present invention generally includes the steps of providing a conductive flexible member having a top side and a bottom side and disposing a non-conductive flexible cover sheet upon the conductive flexible member top side. A connector is provided for establishing electrical contact with an external electrical apparatus and the method includes adhering the connector to the conductive flexible bottom side with a conductive adhesive tape. Thereafter, a conductive adhesive is applied to the conductive flexible member bottom side and the conductive adhesive tape.

BRIEF DESCRIPTION OF THE DRAWINGS

The present invention may be better understood with reference to the following detailed description, taken in conjunction with the accompanying drawings, in which.

DETAILED DESCRIPTION

Figure 1:
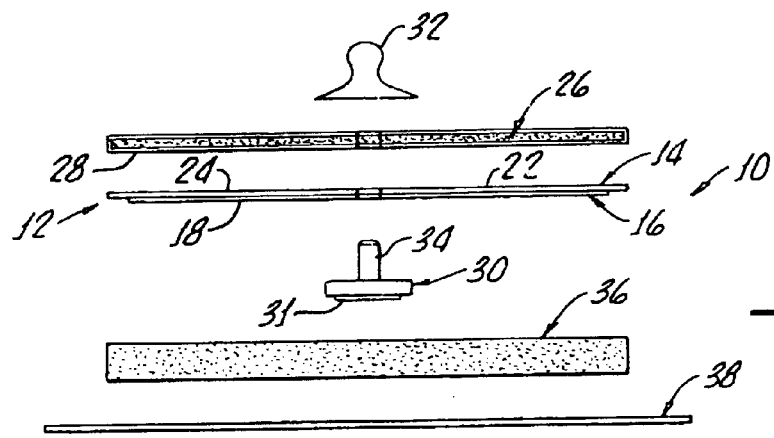
FIG. 1 is an exploded cross-sectional view of medical electrode in accordance with the present invention generally showing a conductive flexible member having a top side and a bottom side, a non-conductive flexible sheet covering the conductive flexible member top side and a connecter, in the form of an eyelet and snap stud along with a conductive hydrogel adhesive and a plastic carrier for preventing premature and inadvertent contact with the hydrogel.

With reference to FIG. 1, there is shown a medical electrode in accordance with the present invention which general includes a conductive flexible member 12 which comprises a conductive film 14 with a conductive ink pattern 16 disposed on a bottom 18 of the conductive film 14, a second conductive ink pattern 22 may be disposed on a top side 24 of the conductive film 14.

A non-conductive flexible sheet 26 covers the conductive flexible member 12 top side 24 and is adhered thereto by an adhesive layer 28. A connector, which may be an eyelet 30, in connect with the conductive member 12, which in combination with a snap stud 32 fixed to a shaft 34 of the eyelet 30, provides a means for establishing electrical contact with an external electrical apparatus, not shown. The shaft 34 extends through the conductive member 12 and the non-conductive flexible sheet 26.

The eyelet 30 is in electrical contact with a conducive hydrogel adhesive 36 which is utilized for adhering the electrode 10 to a patient's skin, not shown. A plastic carrier 38 may be provided in order to prevent inadvertent and/or premature adhesion of a patient's skin or other object to the hydrogel. The plastic carrier 38 is removed prior to application of the electrode 10 to the patient's skin.

Figure 2:
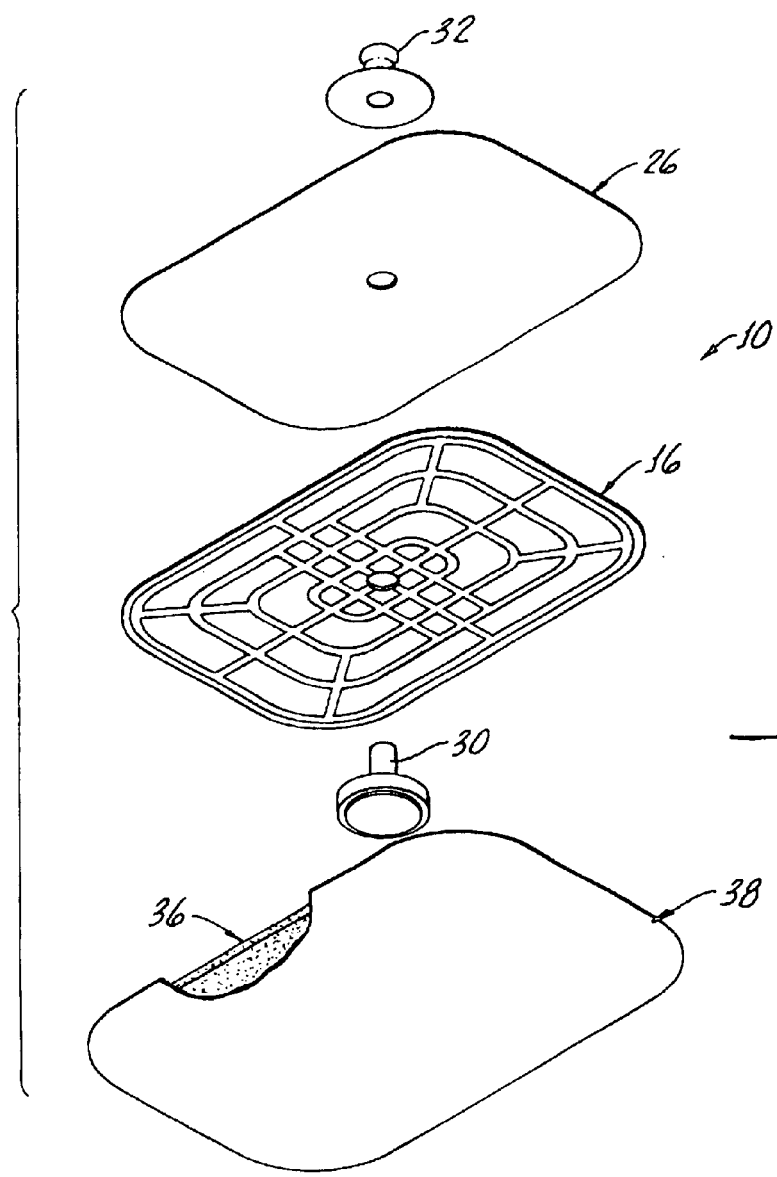
FIG. 2 in an exploded perspective view of the electrode shown in FIG. 1 more clearly showing the conductive member as including a conductive film with a conductive ink pattern disposed thereon.
Figure 3A:
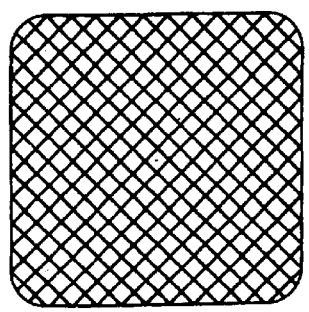
FIGS. 3A–3H illustrate various patterns which may be useful for the ink distribution on the conductive film.
Figure 3B:
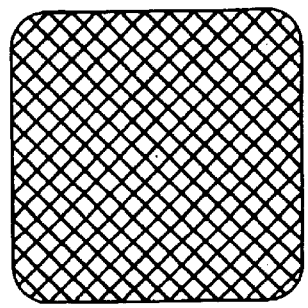
Figure 3C:
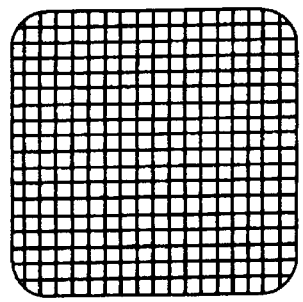
Figure 3D:
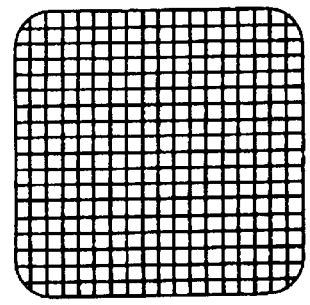
Figure 3E:
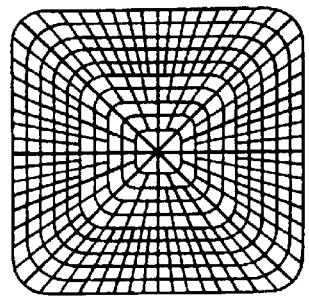
Figure 3F:
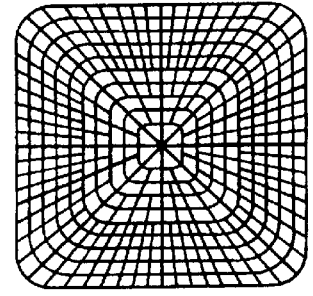
Figure 3G:
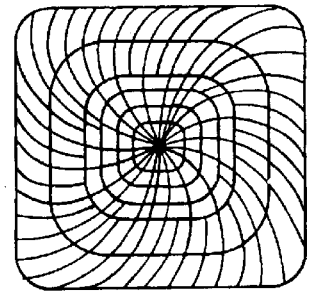
Figure 3H:
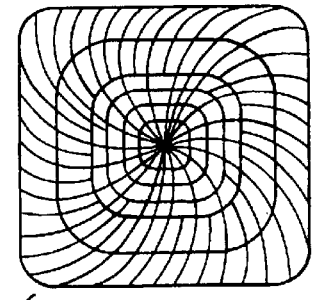

The conductive film 14 may comprise PVC and the ink pattern 16, most clearly shown in FIG. 2, may be of silver. Various patterns such as those shown in FIGS. 3A–3H may be utilized to tailor the current distribution of the electrode 10.

Figure 4:
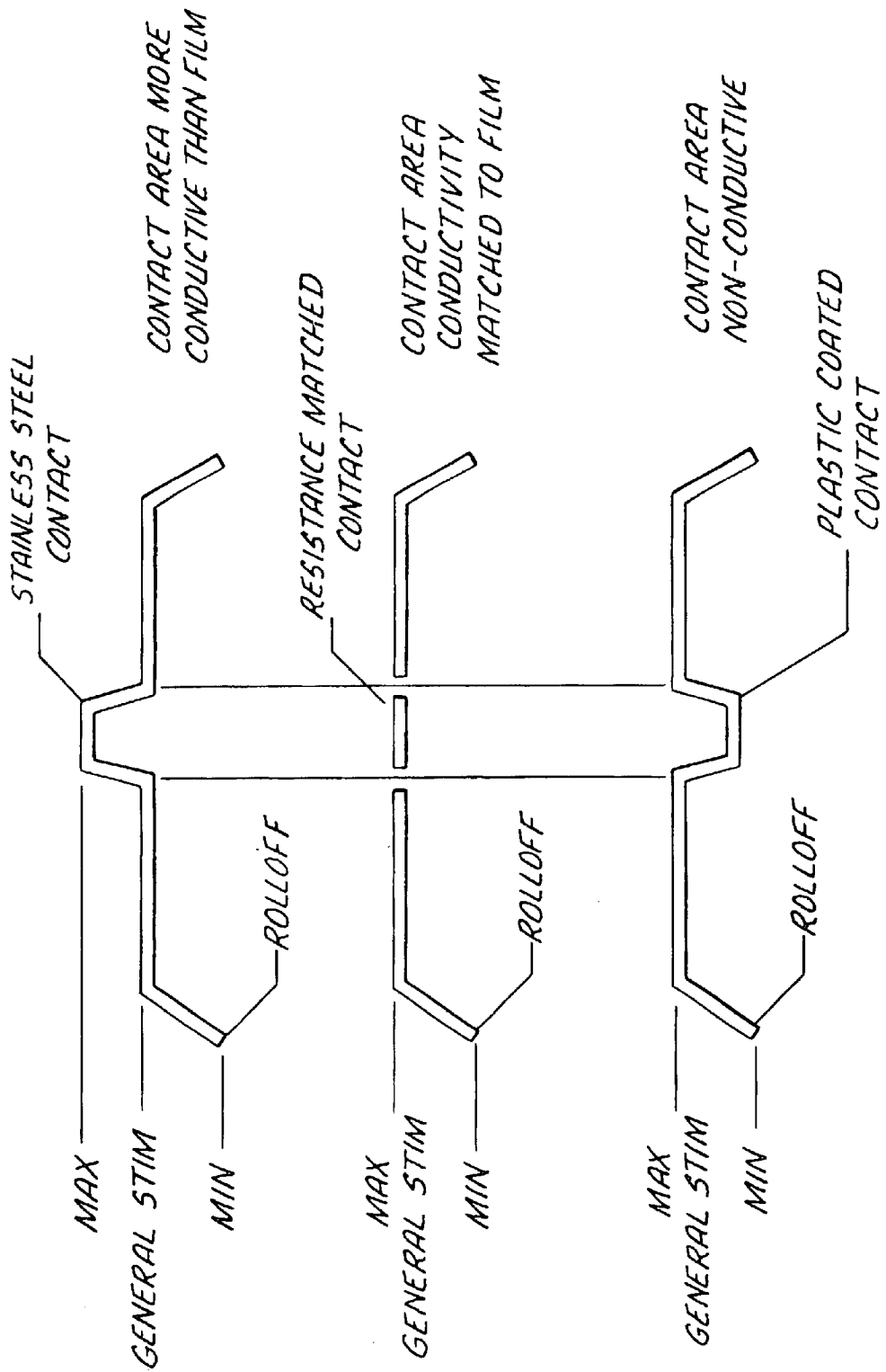
FIG. 4 is a plot of current distribution profile utilizing eyelets of different conductivities.

Importantly, the eyelet 30 may be formed from an electrically conductive material selected to match the conductivity of the conductive flexible member 12. This is accomplished through the use of carbon fibers or particles disposed in a plastic base material. Alternatively, the eyelet may be less conductive or more conductive than the member 12. To provide, if desired, a "non-conductive" eyelet 30, the eyelet may be provided with a coat 31 of plastic. In this manner, the eyelet 30, provides electrical control with the pattern 16, 22 while presenting a non-conductive surface to the hydrogel 36. FIG. 4 shows the current distribution profiles for contacts between the film and the gel utilizing a stainless steel eyelet, a carbon loaded plastic eyelet and a plastic coated eyelet.

Figure 5:
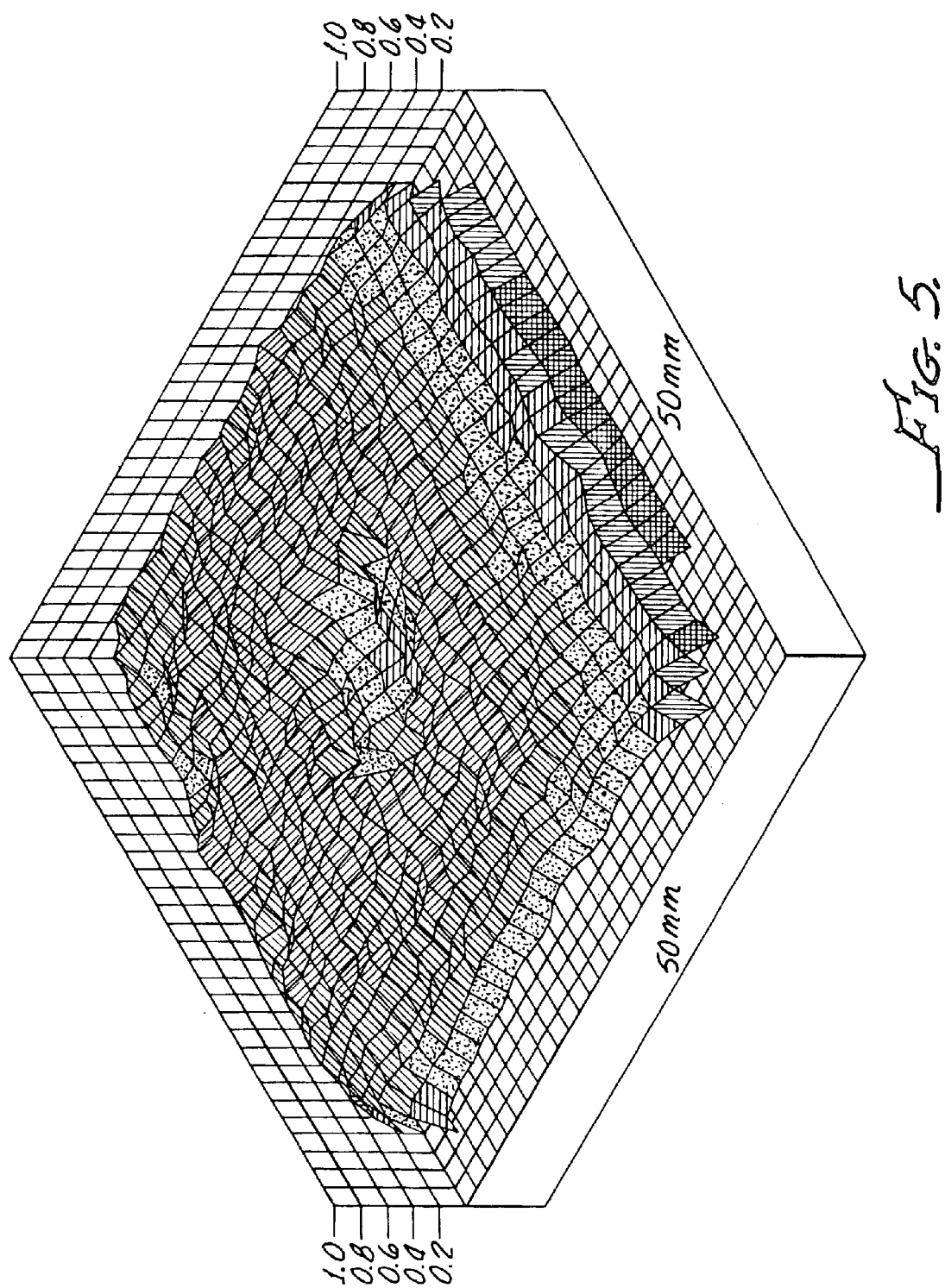
FIGS. 5 and 6 are three dimensional representations of current distribution of the electrode shown in FIG. 1 with different eyelet conductivities.
Figure 6:
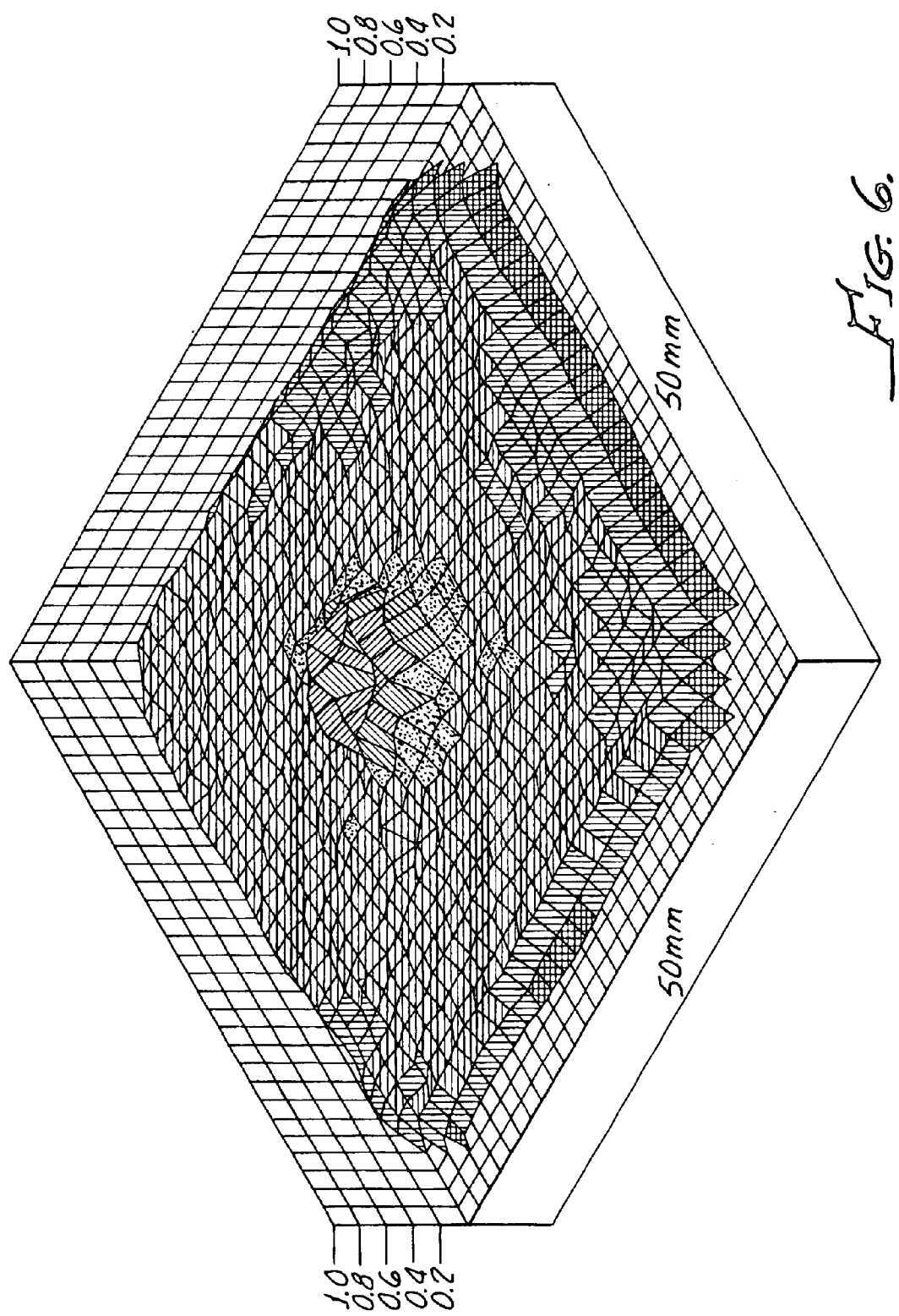

Three dimensional representation are shown in FIGS. 5 and 6.

With references again to FIG. 1, as hereinabove noted, a second conductive ink pattern 22 may be disposed on the top 24 of the conductive member 12 in order to further profile the current density of the electrode 10. The first and second ink patterns 16, 22 may be of the same type or of a different pattern depending upon specific application.

Figure 7:
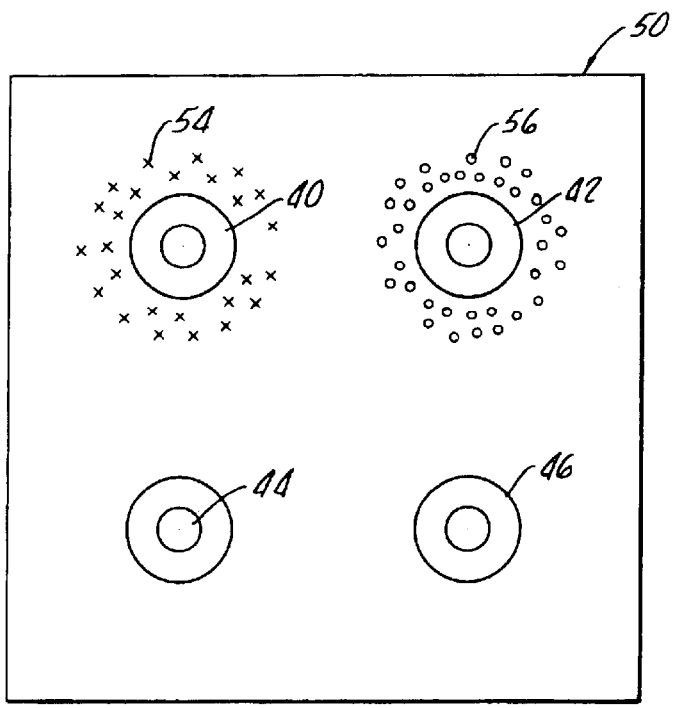
FIG. 7 is a plan view representation of an electrode in accordance with the present invention utilizing a plurality of eyelet connectors.

As shown in FIG. 7, a plurality of eyelets 40, 42, 44, 46 may be utilized with an electrode 50 in order to further tailor the current distribution, or electrical conductivity of the electrode 50 to a desired pattern. Each of the eyelets 40, 42, 44, 46 may have different conductivities, or alternatively, eyelets 40, 42 may be considered one of a set having the same conductivity while eyelets 44, 46 may be considered a different set having different conductivities. It should be appreciated that while only four eyelets are shown for illustration, any number of eyelets may be utilized in accordance with the present invention and spaced in specific patterns depending upon a desired current distribution.

The use of multiple eyelets 40, 42, 44, 46 may also enhance the transcutaneous delivery of drugs into a persons skin, known as iontophoresis and in FIG. 7 representation of such drugs are represented by X's 54 and O's 56.

Figure 8:
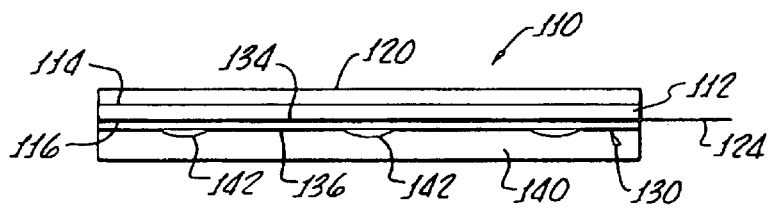
FIG. 8 is a cross-sectional view of an alternative embodiment of a medical electrode in accordance with the present invention generally showing a lead wire intermediate, a conductive member and a conductive adhesive.
Figure 9:
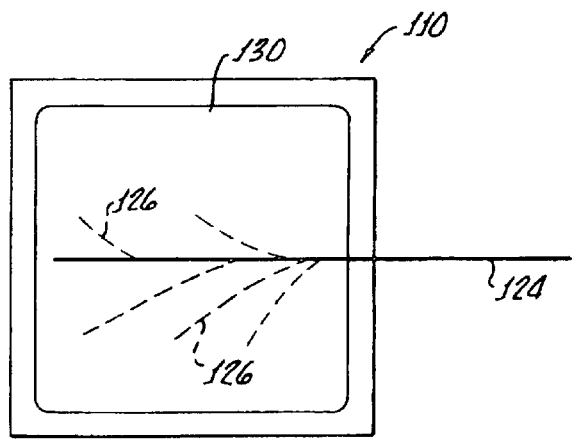
FIG. 9 is a plan view of the electrode shown in FIG. 8.

With reference to FIGS. 8 and 9, there is shown yet another alternate embodiment of a medical electrode 110 in accordance with the present invention generally including a conductive flexible member 112 having a top side 114 and a bottom side 116. The flexible member 112 may be formed from any suitable conductive material such as a conductive fabric or a conductive sheet or a conductive mesh or a suitable conductive foil.

A non-conductive flexible member 120 is disposed on the conductive member top side 114 in order to prevent inadvertent contact with the conductive member 112 which may be electrically charged.

A connector 124 is provided which may be in the form of a single wire as shown in solid line in FIG. 9, or it may comprise several strands 126 of wire shown in dashed line in FIG. 9, which may be spread in order to distribute electrical pulses to the conductive member 112 or vary the overall conductivity of the electrode 112 in order to vary current density provided by the electrode 110 to a patient's skin (not shown).

Importantly, the connector 112, by way of the strands 126, are adhered to the conductive flexible member bottom side 116 by means of a conductive tape 130. The tape 130 may include a conductive adhesive 134 and a conductive backing 136. The conductive backing 136 may be any suitable conductive material such as a metallic foil or a conductive polymer, all well known in the art. In addition, the tape adhesive 34 is conductive and is also well known in the art.

The conductive adhesive 140 provides a means for electrically coupling the electrode 110 to a patient's skin (not shown) and the adhesive 140 may be any suitable type, as for example, a hydrogel which may be layered, as set forth in U.S. Pat. No. 6,038,464 entitled, MEDICAL ELECTRODE AND METHOD OF MANUFACTURE. This patent application is incorporated by this reference thereto in its entirety for describing the type of gel and general electric configuration which may be used to advantage in accordance with the present invention.

With reference to FIG. 9, the conductive tape may include a shape distinct from the electrode 124 or placement of strands 126 in order to provide a means for controlling the overall conductivity of the electrode 110. This control, of course, may be utilized in combination with other methods for controlling electrode conductivity hereinabove mentioned.

In addition to the shape of the conductive tape 130, portions of the conductive tape 130 may be of varying thickness as illustrated by the nodes 142 as shown in FIG. 8. That is, by varying the thickness of the conductive tape further enables tailoring of the overall conductivity of the electrode 110. It should be kept in mind that the conductive tape may be more conductive than the conductive member 112 or less conductive than or equal to the conductive member 112, depending upon the overall arrangement of the electrode and the shape of the conductive tape 130.

A method in accordance with the present invention is also evidenced by FIGS. 8 and 9. Specifically, the method of the present invention includes the providing of an electrical flexible member 112 having a top side 114 and a bottom side 116.

Further, the method includes disposing a non-conductive flexible cover sheet 120 onto the conductive flexible member top surface 114 and providing a connector 124 for establishing electrical contact with an external electrical apparatus (not shown).

Importantly, in accordance with the present invention, the connector 124 is adhered to the flexible member bottom side 116 with the conductive adhesive tape 130 and the conductive adhesive 140 is adhered to the conductive flexible member bottom side 116 and conductive tape 130 for providing electrical conductivity to a patient's skin.

Although there has been described hereinabove a specific medical electrode and method for making same, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the invention as defined in the appended claims.

What is claimed is:

1. A medical electrode comprising:
   a conductive flexible member having a top side and a bottom side;
   a non-conductive flexible sheet covering the conductive flexible member top side;
   a connector, in contact with the conductive flexible member bottom side, for establishing electrical contact with an external electrical apparatus, said connector comprising a snap eyelet having a head in contact with said conductive flexible member and a shaft extending through said conductive flexible member and said non-conductive flexible sheet and a snap stud fixed to the eyelet shaft, the eyelet head being formed from an electrically conductive material selected to match the conductivity of the conductive flexible member; and
   a conductive hydrogel adhesive disposed on the conductive flexible member bottom side for adhering the electrode to a patient's skin.

2. The medical electrode according to claim 1 wherein the eyelet head is formed from a material having greater conductivity than the conductivity of said conductive flexible member.

3. The medical electrode according to claim 1 wherein the eyelet head is formed from a material having lower conductivity than the conductivity of said conductive flexible member.

4. The medical electrode according to claim 1 wherein said connector comprises a plurality of spaced apart snap eyelets each having a head in control with said conductive flexible member and a shaft extending through said conductive flexible member and said non-conductive flexible member and said non-conductive flexible sheet and a plurality of snap stands, one each fixed to each of said plurality of snap eyelet shafts.

5. The medical electrode according to claim 4 wherein each of said plurality of snap eyelets has a different conductivity.

6. The medical electrode according to claim 4 wherein said plurality of snap eyelet include sets of snap eyelets, eyelets in each set having the same conductivity.

7. The medical electrode according to any one of claims 1 and 2–6 wherein said conductive flexible member comprises conductive film with a conductive ink pattern disposed.

8. The medical electrode according to claim 7 wherein the ink pattern has greater conductivity than the conductivity of said conductive film.

9. The medical electrode according to any one of claims 1 and 2–6 wherein said conductive flexible member comprises a conductive film with a first conductive ink pattern disposed on the member bottom side and a second conductive ink pattern disposed on the member top side.

10. The medical electrode according to claim 9 wherein each ink pattern has a conductivity greater than the conductivity of said conductive film.

11. A medical electrode comprising:
   a conductive flexible member having a top side and a bottom side;
   a non-conductive flexible sheet covering the conductive flexible member top side;
   a connector means for establishing electrical contact with an external electrical apparatus;
   a conductive tape means for adhering said connector means to the conductive flexible member bottom side; and
   a conductive adhesive means, adhered to the conductive flexible member bottom side and conductive tape, for providing electrical conductivity to a patient's skin.

12. The medical electrode according to claim 11 wherein said conductive tape comprises a conductive backing and a conductive adhesive disposed between the conductive flexible member bottom side and said conductive backing.

13. The medical electrode according to claim 12 wherein said conductive backing comprises a metallic foil.

14. The medical electrode according to claim 12 wherein said conductive backing comprises a conductive polymer.

15. The medical electrode according to claim 12 wherein said conductive backing and conductive adhesive have a conductivity less than a conductivity of said conductive flexible member.

16. The medical electrode according to claim 12 wherein said conductive backing and conductive adhesive have a conductivity greater than a conductivity of said conductive flexible member.

17. The medical electrode according to claim 16 wherein said conductive tape is wider than said connector.

18. The medical electrode according to claim 17 wherein said conductive tape includes means for controlling overall conductivity of the medical electrode.

19. The medical electrode according to claim 18 wherein said means for controlling overall conductivity comprises a selected shape of said conductive tape.

20. The medical electrode according to claim 19 wherein said means for controlling overall conductivity further comprises a varying thickness of said conductive tape.

21. A method for making a medical electrode comprises the steps of:
   providing a conductive flexible member having a top side and a bottom side;
   disposing a non-conductive flexible cover sheet upon the conductive flexible member top side;
   providing a connector for establishing electrical contact with an external electrical apparatus;
   adhering said connector to the conductive flexible member bottom side with a conductive adhesive tape; and
   applying a conductive adhesion to the conductive flexible member bottom side and said conductive adhesive tape.

* * * * *